(12) United States Patent
Cheung et al.

(10) Patent No.: US 7,728,016 B2
(45) Date of Patent: Jun. 1, 2010

(54) SUBSTITUTED 5-MEMBERED RING COMPOUNDS AND THEIR USE

(75) Inventors: Kwai Ming Cheung, London (GB); Brian William Dymock, Abingdon (GB); Edward McDonald, London (GB); Martin James Drysdale, Abington (GB)

(73) Assignees: Vernalis (Cambridge) Limited (GB); Cancer Research Technology Ltd. (GB); Institute of Cancer Research (GB)

( * ) Notice: Subject to any disclaimer, the term of this patent is extended or adjusted under 35 U.S.C. 154(b) by 0 days.

(21) Appl. No.: 10/561,969

(22) PCT Filed: Jun. 24, 2004

(86) PCT No.: PCT/GB2004/002755

§ 371 (c)(1),
(2), (4) Date: Apr. 10, 2006

(87) PCT Pub. No.: WO2005/000300

PCT Pub. Date: Jan. 6, 2005

(65) Prior Publication Data

US 2006/0235058 A1    Oct. 19, 2006

(30) Foreign Application Priority Data

Jun. 27, 2003    (GB) .................. 0315111.5

(51) Int. Cl.
*A61K 31/4192*    (2006.01)
*C07D 249/06*    (2006.01)

(52) U.S. Cl. ....................... 514/359; 548/255

(58) Field of Classification Search ................. 514/359; 548/255

See application file for complete search history.

(56) References Cited

U.S. PATENT DOCUMENTS 5,489,598 A    2/1996 Connor et al.
5,869,509 A    2/1999 Gribkoff et al.

FOREIGN PATENT DOCUMENTS

| DE | 4320801 | 1/1995 |
|---|---|---|
| EP | 1 070 708 | 1/2001 |
| EP | 1 293 503 | 3/2003 |
| FR | 2 258 180 | 8/1975 |
| GB | 1 406 345 | 9/1975 |
| WO | 99-40088 | 8/1999 |
| WO | 99-64415 | 12/1999 |
| WO | 01-07436 | 2/2001 |
| WO | 01-34198 | 5/2001 |
| WO | 01-34580 | 5/2001 |
| WO | 03-015777 | 2/2003 |
| WO | 03-101985 | 12/2003 |
| WO | 03-104207 | 12/2003 |
| WO | 2004-030611 | 4/2004 |

OTHER PUBLICATIONS

Abstract of Afinidad (1993), 50(447), pp. 316-318, from STN search report.*
Medaer et al., Tetrahedron, 1997, 52(26), pp. 8813-8826.*
Vippagunta et al., Advanced Drug Delivery Reviews, p. 1.*
Fevig John M. et al: "Synthesis and SAR of benzamidine factor Xa inhibitors containing a vicinally-substituted heterocyclic core" Bioorganic and Medicinal Chemistry Letters, vol. 11, No. 5, Mar. 12, 2001, XP002301746, ISSN: 0960-894X.

* cited by examiner

*Primary Examiner*—Yong Chu
(74) *Attorney, Agent, or Firm*—Banner & Witcoff, Ltd.

(57) ABSTRACT

Compound of a compound of formula (I) or a salt, N-oxide, hydrate or solvate thereof, in the preparation of a composition for inhibition of HSP90 activity: wherein ring A is an aromatic or non-aromatic carbocyclic or heterocyclic ring having 5 ring atoms, for example 1,2,3-triazolyl or a 1,2,4-triazolyl or a tetrazolyl ring; and $R_1$ $R_2$ $R_3$ are as defined in the specification are inhibitors of HSP90 and therefore of use in the treatment of, for example, cancers, viral disease, inflammatory diseases such as rheumatoid arthritis, asthma, multiple sclerosis, Type I diabetes, lupus, psoriasis and inflammatory bowel disease; cystic fibrosis angiogenesis-related disease such as diabetic retinopathy, haemangiomas, and endometriosis; or for protection of normal cells against chemotherapy-induced toxicity; or diseases where failure to undergo apoptosis is an underlying factor, or protection from hypoxia-ischemic injury due to elevation of Hsp70 in the heart and brain; scrapie/CJD, Huntingdon's and Alzheimer's disease.

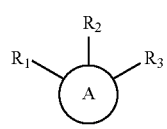

(I)

6 Claims, No Drawings

US 7,728,016 B2

SUBSTITUTED 5-MEMBERED RING COMPOUNDS AND THEIR USE

This application is a U.S. National Stage application of co-pending PCT application PCT/GB2004/002755, filed Jun. 24, 2004, which claims the priority of Great Britain Patent Application No. 0315111.5, filed Jun. 27, 2003. These applications are incorporated herein by reference in their entireties.

This invention relates to substituted 5-membered ring compounds (carbocyclic and heterocyclic compounds having 5 ring atoms) having HSP90 inhibitory activity, to the use of such compounds in medicine, in relation to diseases which are mediated by excessive or inappropriate HSP90 activity such as cancers, and to pharmaceutical compositions containing such compounds.

BACKGROUND OF THE INVENTION

Molecular chaperones maintain the appropriate folding and conformation of proteins and are crucial in regulating the balance between protein synthesis and degradation. They have been shown to be important in regulating many important cellular functions, such as cell proliferation and apoptosis (Jolly and Morimoto, 2000; Smith et al., 1998; Smith, 2001).

Heat Shock Proteins (HSPs)

Exposure of cells to a number of environmental stresses, including heat shock, alcohols, heavy metals and oxidative stress, results in the cellular accumulation of a number of chaperones, commonly known as heat shock proteins (HSPs). Induction of HSPs protects the cell against the initial stress insult, enhances recovery and leads to maintenance of a stress tolerant state. It has also become clear, however, that certain HSPs may also play a major molecular chaperone role under normal, stress-free conditions by regulating the correct folding, degradation, localization and function of a growing list of important cellular proteins.

A number of multigene families of HSPs exist, with individual gene products varying in cellular expression, function and localization. They are classified according to molecular weight, e.g., HSP70, HSP90, and HSP27.

Several diseases in humans can be acquired as a result of protein misfolding (reviewed in Tytell et al., 2001; Smith et al., 1998). Hence the development of therapies which disrupt the molecular chaperone machinery may prove to be beneficial. In some conditions (e.g., Alzheimer's disease, prion diseases and Huntington's disease), misfolded proteins can cause protein aggregation resulting in neurodegenerative disorders. Also, misfolded proteins may result in loss of wild type protein function, leading to deregulated molecular and physiological functions in the cell.

HSPs have also been implicated in cancer. For example, there is evidence of differential expression of HSPs which may relate to the stage of tumour progression (Martin et al., 2000; Conroy et al., 1996; Kawanishi et al., 1999; Jameel et al., 1992; Hoang et al., 2000; Lebeau et al., 1991). As a result of the involvement of HSP90 in various critical oncogenic pathways and the discovery that certain natural products with anticancer activity are targeting this molecular chaperone, the fascinating new concept has been developed that inhibiting HSP function may be useful in the treatment of cancer. The first molecular chaperone inhibitor is currently undergoing clinical trials.

HSP90

HSP90 constitutes about 1-2% of total cellular protein, and is usually present in the cell as a dimer in association with one of a number of other proteins (see, e.g., Pratt, 1997). It is essential for cell viability and it exhibits dual chaperone functions (Young et al., 2001). It plays a key role in the cellular stress response by interacting with many proteins after their native conformation has been altered by various environmental stresses, such as heat shock, ensuring adequate protein folding and preventing non-specific aggregation (Smith et al., 1998). In addition, recent results suggest that HSP90 may also play a role in buffering against the effects of mutation, presumably by correcting the inappropriate folding of mutant proteins (Rutherford and Lindquist, 1998). However, HSP90 also has an important regulatory role. Under normal physiological conditions, together with its endoplasmic reticulum homologue GRP94, HSP90 plays a housekeeping role in the cell, maintaining the conformational stability and maturation of several key client proteins. These can be subdivided into three groups: (a) steroid hormone receptors, (b) Ser/Thr or tyrosine kinases (e.g., ERBB2, RAF-1, CDK4, and LCK), and (c) a collection of apparently unrelated proteins, e.g., mutant p53 and the catalytic subunit of telomerase hTERT. All of these proteins play key regulatory roles in many physiological and biochemical processes in the cell. New HSP90 client proteins are continuously being identified.

The highly conserved HSP90 family in humans consists of four genes, namely the cytosolic HSP90α and HSP90β isoforms (Hickey et al., 1989), GRP94 in the endoplasmic reticulum (Argon et al., 1999) and HSP75/TRAP1 in the mitochondrial matrix (Felts et al., 2000). It is thought that all the family members have a similar mode of action, but bind to different client proteins depending on their localization within the cell. For example, ERBB2 is known to be a specific client protein of GRP94 (Argon et al., 1999) and type 1 tumour necrosis factor receptor (TNFR1) and RB have both been shown to be clients of TRAP1 (Song et al., 1995; Chen et al., 1996).

HSP90 participates in a series of complex interactions with a range of client and regulatory proteins (Smith, 2001). Although the precise molecular details remain to be elucidated, biochemical and X-ray crystallographic studies (Prodromou et al., 1997; Stebbins et al., 1997) carried out over the last few years have provided increasingly detailed insights into the chaperone function of HSP90.

Following earlier controversy on this issue, it is now clear that HSP90 is an ATP-dependent molecular chaperone (Prodromou et al, 1997), with dimerization of the nucleotide binding domains being essential for ATP hydrolysis, which is in turn essential for chaperone function (Prodromou et al, 2000a). Binding of ATP results in the formation of a toroidal dimer structure in which the N terminal domains are brought into closer contact with each other resulting in a conformational switch known as the 'clamp mechanism' (Prodromnou and Pearl, 2000b).

Known HSP90 Inhibitors

The first class of HSP90 inhibitors to be discovered was the benzoquinone ansamycin class, which includes the compounds herbimycin A and geldanamycin. They were shown to reverse the malignant phenotype of fibroblasts transformed by the v-Src oncogene (Uehara et al., 1985), and subsequently to exhibit potent antitumour activity in both in vitro (Schulte et al., 1998) and in vivo animal models (Supko et al., 1995).

Immunoprecipitation and affinity matrix studies have shown that the major mechanism of action of geldanamycin involves binding to HSP90 (Whitesell et al., 1994; Schulte and Neckers, 1998). Moreover, X-ray crystallographic studies have shown that geldanamycin competes at the ATP binding site and inhibits the intrinsic ATPase activity of HSP90 (Prodromou et al., 1997; Panaretou et al., 1998). This in turn prevents the formation of mature multimeric HSP90 complexes capable of chaperoning client proteins. As a result, the client proteins are targeted for degradation via the ubiquitin proteasome pathway. 17-Allylamino, 17-demethoxygeldanamycin (17AAG) retains the property of HSP90 inhibition resulting in client protein depletion and antitumour activity in cell culture and xenograft models (Schulte et al, 1998; Kelland et al, 1999), but has significantly less hepatotoxicity than geldanamycin (Page et al, 1997). 17AAG is currently being evaluated in Phase I clinical trials.

Radicicol is a macrocyclic antibiotic shown to reverse the malignant phenotype of v-Src and v-Ha-Ras transformed fibroblasts (Kwon et al, 1992; Zhao et al, 1995). It was shown to degrade a number of signalling proteins as a consequence of HSP90 inhibition (Schulte et al., 1998). X-ray crystallographic data confirmed that radicicol also binds to the N terminal domain of HSP90 and inhibits the intrinsic ATPase activity (Roe et al., 1998). Radicicol lacks antitumour activity in vivo due to the unstable chemical nature of the compound.

Coumarin antibiotics are known to bind to bacterial DNA gyrase at an ATP binding site homologous to that of the HSP90. The coumarin, novobiocin, was shown to bind to the carboxy terminus of HSP90, i.e., at a different site to that occupied by the benzoquinone ansamycins and radicicol which bind at the N-terminus (Marcu et al., 2000b). However, this still resulted in inhibition of HSP90 function and degradation of a number of HSP90-chaperoned signalling proteins (Marcu et al., 2000a). Geldanamcyin cannot bind HSP90 subsequent to novobiocin; this suggests that some interaction between the N and C terminal domains must exist and is consistent with the view that both sites are important for HSP90 chaperone properties.

A purine-based HSP90 inhibitor, PU3, has been shown to result in the degradation of signalling molecules, including ERBB2, and to cause cell cycle arrest and differentiation in breast cancer cells (Chiosis et al., 2001).

HSP90 as a Therapeutic Target

Due to its involvement in regulating a number of signalling pathways that are crucially important in driving the phenotype of a tumour, and the discovery that certain bioactive natural products exert their effects via HSP90 activity, the molecular chaperone HSP90 is currently being assessed as a new target for anticancer drug development (Neckers et al., 1999).

The predominant mechanism of action of geldanamycin, 17AAG, and radicicol involves binding to HSP90 at the ATP binding site located in the N-terminal domain of the protein, leading to inhibition of the intrinsic ATPase activity of HSP90 (see, e.g., Prodromou et al., 1997; Stebbins et al., 1997; Panaretou et al., 1998).

Inhibition of HSP90 ATPase activity prevents recruitment of co-chaperones and encourages the formation of a type of HSP90 heterocomplex from which these client proteins are targeted for degradation via the ubiquitin proteasome pathway (see, e.g., Neckers et al., 1999; Kelland et al., 1999).

Treatment with HSP90 inhibitors leads to selective degradation of important proteins involved in cell proliferation, cell cycle regulation and apoptosis, processes which are fundamentally important in cancer.

Inhibition of HSP90 function has been shown to cause selective degradation of important signalling proteins involved in cell proliferation, cell cycle regulation and apoptosis, processes which are fundamentally important and which are commonly deregulated in cancer (see, e.g., Hostein et al., 2001). An attractive rationale for developing drugs against this target for use in the clinic is that by simultaneously depleting proteins associated with the transformed phenotype, one may obtain a strong antitumour effect and achieve a therapeutic advantage against cancer versus normal cells. These events downstream of HSP90 inhibition are believed to be responsible for the antitumour activity of HSP90 inhibitors in cell culture and animal models (see, e.g., Schulte et al., 1998; Kelland et al., 1999).

BRIEF DESCRIPTION OF THE INVENTION

In copending patent applications nos. PCT/GB02/005778, GB0228417.2, GB0229618.4 and GB0309637.7, it has been shown that certain substituted pyrazoles and isoxazoles are inhibitors of HSP90 activity. Analogues of those compounds, wherein the pyrazole or isoxazole ring is replaced by other 5-membered ring systems are conformationally similar and expected to have HSP90 inhibitory activity. The present invention relates to the use of such analogous substituted 5-membered ring compounds as HSP90 inhibitors, for example for inhibition of cancer cell proliferation. A core 5-membered ring with aromatic substitution on one ring carbon atom are principle characterising features of the compounds with which the invention is concerned.

DETAILED DESCRIPTION OF THE INVENTION

According to the present invention there is provided the use of a compound of formula (I) or a salt, N-oxide, hydrate or solvate thereof, in the preparation of a composition for inhibition of HSP90 activity:

(I)

wherein ring A is an aromatic or non-aromatic carbocyclic or heterocyclic ring having 5 ring atoms;

$R_1$ is attached to a first ring atom of ring A and is a group of formula (IA):

(IA)

wherein in any compatible combination $Ar^1$ is an optionally substituted aryl or heteroaryl radical, $Alk^1$ and $Alk^2$ are optionally substituted divalent $C_1$-$C_6$ alkylene or $C_2$-$C_6$ alkenylene radicals, p, r and s are independently 0 or 1, Z is —O—, —S—, —(C=O)—, —(C=S)—, —$SO_2$—, —C(=O)O—, —C(=O)$NR^4$—, —C(=S)$NR^4$—, —SO$_2$NR$^A$—, —NR$^A$C(=O)—, —NR$^A$SO$_2$— or —NR$^A$— wherein R$^A$ is hydrogen or C$_1$-C$_6$ alkyl, and Q is hydrogen or an optionally substituted carbocyclic or heterocyclic radical;

R$_2$ is attached to a second ring atom of ring A, which is adjacent the first ring atom to which R$_1$ is attached, or is absent if that ring atom is a nitrogen atom which is double bonded to a neighbouring ring atom, and if not absent R$_1$ is hydrogen or
 (i) a group of formula (IA) as defined in relation to R$_1$;
 (ii) a carboxamide radical; or
 (iii) a non aromatic carbocyclic or heterocyclic ring wherein a ring carbon is optionally substituted, and/or a ring nitrogen is optionally substituted by a group of formula -(Alk$^1$)$_p$-(Z)$_r$-(Alk$^2$)$_s$-Q wherein Q, Alk$^1$, Alk$^2$, Z, p, r and s are as defined above in relation to group (IA); and R$_3$ is attached to a third ring atom of ring A, which is adjacent the second ring atom to which R$_2$ is attached, or is absent if that ring atom is a nitrogen atom which is double bonded to a neighbouring ring atom, and if not absent R$_2$ is hydrogen, optionally substituted cycloalkyl, cycloalkenyl, C$_1$-C$_6$ alkyl, C$_1$-C$_6$ alkenyl, or C$_1$-C$_6$ alkynyl; or a carboxyl, carboxamide or carboxyl ester group, PROVIDED THAT (a) at least one of R$_2$ and R$_3$ is present and is other than hydrogen and (b) the compound of formula (I) is not one of formula (IA) (IB), (IC) or (ID)

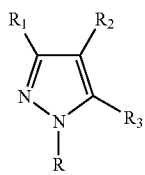
(IA)

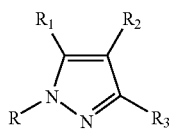
(IB)

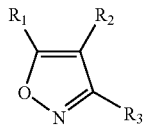
(IC)

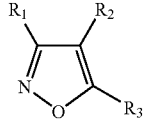
(ID)

wherein R$_1$, R$_2$, and R$_3$ are as defined above, and R is hydrogen or optionally substituted C$_1$-C$_6$ alkyl.

Many compounds and sub-classes of the class of compounds defined above in relation to formula (I) is believed to be novel, and the invention includes all novel members of that class and their salts, hydrates and solvates.

As used herein:
 the term "carboxyl group" refers to a group of formula —COOH;
 the term "carboxyl ester group" refers to a group of formula —COOH, wherein R is a radical actually or notionally derived from the hydroxyl compound ROH; and
 the term "carboxamide group" refers to a group of formula —CONR$_a$R$_b$, wherein —NR$_a$R$_b$ is a primary or secondary (including cyclic) amino group actually or notionally derived from ammonia or the amine HNR$_a$R$_b$.

As used herein, the term "(C$_1$-C$_6$)alkyl" refers to a straight or branched chain alkyl radical having from 1 to 6 carbon atoms, including for example, methyl, ethyl, n-propyl, isopropyl, n-butyl, isobutyl, sec-butyl, t-butyl, n-pentyl and n-hexyl.

As used herein the term "divalent (C$_1$-C$_6$)alkylene radical" means a saturated hydrocarbon chain having from 1 to 6 carbon atoms and two unsatisfied valences.

As used herein, the term "(C$_1$-C$_6$)alkenyl" refers to a straight or branched chain alkenyl radical having from 2 to 6 carbon atoms and containing at least one double bond of E or Z configuration, including for example, ethenyl and allyl.

As used herein the term "divalent (C$_2$-C$_6$)alkenylene radical" means a hydrocarbon chain having from 2 to 6 carbon atoms, at least one double bond, and two unsatisfied valences.

As used herein, the term "(C$_1$-C$_6$)alkynyl" refers to a straight or branched chain alkenyl radical having from 2 to 6 carbon atoms and containing at least one triple bond, including for example, ethynyl and prop-2-ynyl.

As used herein the term "cycloalkyl" refers to a saturated carbocyclic radical having from 3-8 carbon atoms and includes, for example, cyclopropyl, cyclobutyl, cyclopentyl, cyclohexyl, cycloheptyl and cyclooctyl.

As used herein the term "cycloalkenyl" refers to a carbocyclic radical having from 3-8 carbon atoms containing at least one double bond, and includes, for example, cyclopentenyl, cyclohexenyl, cycloheptenyl and cyclooctenyl.

As used herein the term "aryl" refers to a mono-, bi- or tri-cyclic carbocyclic aromatic radical. Illustrative of such radicals are phenyl, biphenyl and napthyl.

As used herein the term "carbocyclic" refers to a cyclic radical whose ring atoms are all carbon, and includes monocyclic aryl, cycloalkyl and cycloalkenyl radicals.

As used herein the term "heteroaryl" refers to a mono-, bi- or tri-cyclic aromatic radical containing one or more heteroatoms selected from S, N and O. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in particular means a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with at least one substituent selected from (C$_1$-C$_6$)alkyl, (C$_1$-C$_6$)alkoxy, hydroxy, hydroxy(C$_1$-C$_6$)alkyl, mercapto, mercapto(C$_1$-C$_6$)alkyl, (C$_1$-C$_6$)alkylthio, halo (including fluoro and chloro), trifluoromethyl, trifluoromethoxy, nitro, nitrile (—CN), oxo, phenyl, —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$, or —NR$^A$CONR$^A$R$^B$ wherein R$^A$ and R$^B$ are independently a (C$_1$-C$_6$)alkyl group. The term "optional substituent" means one of the foregoing substituent groups.

As used herein the term "salt" includes base addition, acid addition and quaternary salts. Compounds of the invention which are acidic can form salts, including pharmaceutically or veterinarily acceptable salts, with bases such as alkali metal hydroxides, e.g. sodium and potassium hydroxides; alkaline earth metal hydroxides e.g. calcium, barium and magnesium hydroxides; with organic bases e.g. N-ethyl piperidine, dibenzylamine and the like. Those compounds (I) which are basic can form salts, including pharmaceutically or veterinarily acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic and p-toluene sulphonic acids and the like.

Some compounds of the invention contain one or more actual or potential chiral centres because of the presence of asymmetric carbon atoms. The presence of several asymmetric carbon atoms gives rise to a number of diastereoisomers with R or S stereochemistry at each chiral centre. The invention includes all such diastereoisomers and mixtures thereof.

The Ring A

Compounds of formula (I) may include the following, wherein R$_1$, R$_2$ and R$_3$ are as defined herein and X represents O or S:

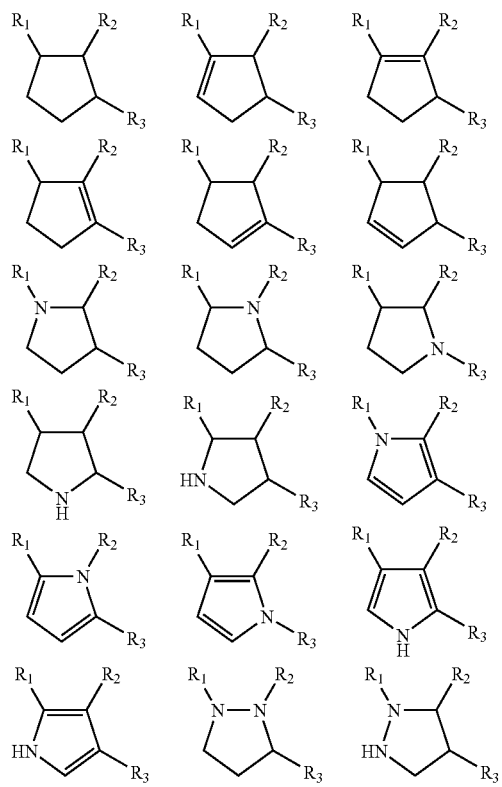

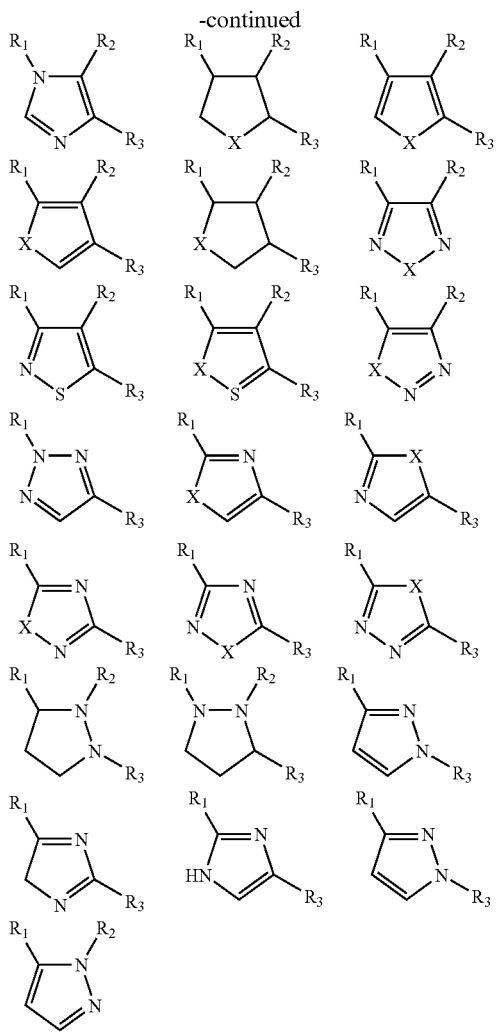

Of the above structures, those wherein the 5-membered ring is aromatic are preferred, for example 1,2,4-tetrazolyl, or 1,2,3-triazole rings.

Specific structures (I) with which the invention is concerned have formulae (IE) and (IF):

(IE)

(IF)

The Radical R$_1$

In general, it is currently preferred that the radical Ar$^1$ present in the R$_1$ group is optionally substituted phenyl, preferably with one of the optional substituents being a hydroxy group in position 2 relative to the point of attachment of the phenyl ring to the 5-membered ring. In other words, the group $R_1$ preferably has formula (IB)

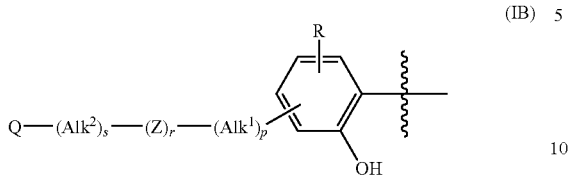
(IB)

wherein $Alk^1$, $Alk^2$, p, r, s, Z and Q are as defined above in relation to $R_1$, and R represents one or optional substituents. In the further discussion of $R_1$ which follows, this preference applies in addition to any other possibilities mentioned.

In the simplest structures with which the invention is concerned, each of p, r and s may be 0, and Q may be hydrogen, so that $R_1$ is optionally substituted aryl or heteroaryl. In such cases, $R_1$ may be, for example, optionally substituted phenyl, preferably 2-hydroxyphenyl which may be further substituted, for example by one or more of hydroxy, methyl, ethyl, methoxy, ethoxy, chloro, or bromo. Currently preferred are compounds wherein $R_1$ is 2,4-dihydroxyphenyl, substituted in the 5-position by hydroxy, methyl, ethyl, methoxy, ethoxy, chloro, or bromo.

In other simple structures, p, r and s may again each be 0, and Q may be an optionally substituted carbocyclic or heterocyclic ring, for example phenyl, cyclohexyl, pyridyl, morpholino, piperidinyl, or piperazinyl ring. In such cases, Q is a direct substituent in the optionally substituted $Ar^1$ ring.

In more complex structures with which the invention is concerned, one or more of p, r and s may be 1, and Q may be hydrogen or an optionally substituted carbocyclic or heterocyclic ring. For example, p and/or s may be 1 and r may be 0, so that Q is linked to $Ar^1$ by an alkylene or alkenylene radical, for example a $C_1$-$C_3$ alkylene radical, which is optionally substituted. In other cases each of p, r, and s may be 1, in which cases, Q is linked to $Ar^1$ by an alkylene or alkenylene radical which is interrupted by the hetero atom-containing Z radical. In still other cases, p and s may be 0 and r may be 1, in which case Q is linked to $Ar^1$ via the hetero atom-containing Z radical.

Specific examples of $R_1$ groups of the above types are present in the compounds of the Examples herein.

The Radical $R_2$

When $R_2$ is of type (i), i.e. a group of formula (IA), examples include phenyl, 2-, 3-, or 4-pyridyl, 2- or 3-furanyl, 2- or 3-thienyl, and thiazolyl wherein optional substituents include any of those listed above in the definition of "substituted", for example methoxy, ethoxy methylenedioxy, ethylenedioxy, fluoro, chloro, bromo, and trifluoromethyl. Currently preferred are compounds wherein R2 is phenyl substituted in the 4 position by $C_1$-$C_6$ alkoxy such as methoxy or ethoxy, fluoro, chloro, bromo, morpholinomethyl, piperazino, N-methylpiperazino, or piperidino When $R_2$ is a carboxamide radical of type (ii) above, examples include those of formula —$CONR^B(Alk)_nR^A$ wherein Alk is a divalent alkylene, alkenylene or alkynylene radical, for example a —$CH_2$—, —$CH_2CH_2$—, —$CH_2CH_2CH_2$—, —$CH_2CH=CH$—, or —$CH_2CCCH_2$— radical, and the Alk radical may be optionally substituted, n is 0 or 1, $R^B$ is hydrogen or a $C_1$-$C_6$ alkyl or $C_2$-$C_6$ alkenyl group, for example methyl, ethyl, n- or iso-propyl, or allyl, $R^A$ is hydroxy or optionally substituted carbocyclic, for example hydroxy and/or chloro-substituted phenyl and 3,4 methylenedioxyphenyl; or heterocyclyl, for example pyridyl, furyl, thienyl, N-piperazinyl, or N-morpholinyl any of which heterocyclic rings may be substituted, or $R^A$ and $R^B$ taken together with the nitrogen to which they are attached form an N-heterocyclic ring which may optionally contain one or more additional hetero atoms selected from O, S and N, and which may optionally be substituted on one or more ring C or N atoms, examples of such N-heterocyclic rings including morpholino, piperidinyl, piperazinyl and N-phenylpiperazinyl.

The Radical $R_3$ $R_3$ may be, for example, hydrogen, methyl, ethyl, n- or iso-propyl, trifluoromethyl, hydroxyethyl or a carboxamide group —$CONR^B(Alk)_nR^A$ as discussed above for $R_2$. Hydrogen, methyl or a carboxamide group are presently preferred.

A particular sub-set of the compounds with which this invention is concerned consists of those of formula (IE) and (IF), and their salts, solvates and hydrates;

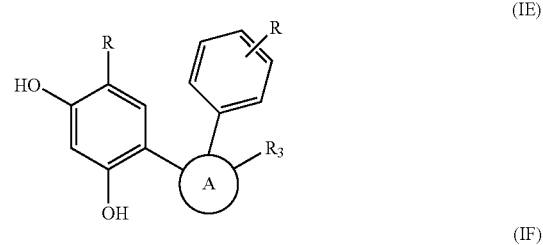
(IE)

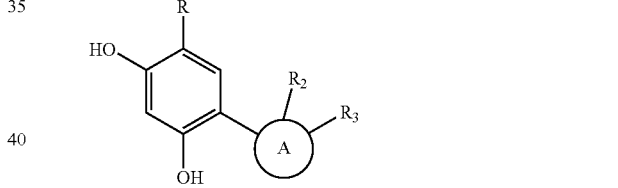
(IF)

wherein each R independently represents an optional substituent and each of $R^2$ and $R^3$ independently represents a carboxamide group.

Another particular sub-set of the compounds with which this invention is concerned consists of those of formula (IG), and their salts, solvates and hydrates:

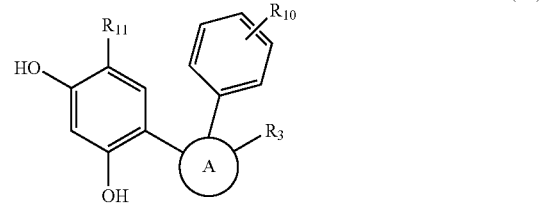
(IG)

wherein $R_3$ represents a carboxamide group (especially an ethylcarboxamide group $CH_3CH_2NHC(=O)$—), $R_{10}$ represents $C_1$-$C_6$ alkoxy such as methoxy or ethoxy, fluoro, chloro, bromo, morpholinomethyl, piperazino, N-methylpiperazino, piperidino, N-methylpiperazinomethyl, or piperidinomethyl, and R$_{11}$ represents bromo, chloro, phenyl, C$_1$-C$_6$ alkyl such as ethyl, iso-propyl, isobutyl or tert-butyl, or phenyl(C$_1$-C$_6$ alkyl)—such as benzyl or phenylethyl.

Specific compounds with which the invention is concerned include those of the Examples.

Compounds with which the invention is concerned may be prepared by literature methods, such as those of the preparative Examples herein, and methods analogous thereto.

The compounds of the invention are inhibitors of HSP90 and are thus useful in the treatment of diseases which are mediated by excessive or inappropriate HSP90 activity such as cancers; viral diseases such as Hepatitis C (HCV) (Waxman, 2002); Immunosupression such as in transplantation (Bijlmakers, 2000 and Yorgin, 2000); Anti-inflammatory diseases (Bucci, 2000) such as Rheumatoid arthritis, Asthma, MS, Type I Diabetes, Lupus, Psoriasis and Inflammatory Bowel Disease; Cystic fibrosis (Fuller, 2000); Angiogenesis-related diseases (Hur, 2002 and Kurebayashi, 2001): diabetic retinopathy, haemangiomas, psoriasis, endometriosis and tumour angiogenesis. Also an Hsp90 inhibitor of the invention may protect normal cells against chemotherapy-induced toxicity and be useful in diseases where failure to undergo apoptosis is an underlying factor. Such an Hsp90 inhibitor may also be useful in diseases where the induction of a cell stress or heat shock protein response could be beneficial, for example, protection from hypoxia-ischemic injury due to elevation of Hsp70 in the heart (Hutter, 1996 and Trost, 1998) and brain (Plumier, 1997 and Rajder, 2000). An Hsp90 inhibitor could also be useful in diseases where protein misfolding or aggregation is a major causal factor, for example, scrapie/CJD, Huntingdon's and Alzheimer's (Sittler, 2001; Trazelt, 1995 and Winklhofer, 2001).

Accordingly, the invention also provides:

(i) a method of treatment of diseases or conditions mediated by excessive or inappropriate HSP90 activity in mammals, particularly humans, which method comprises administering to the mammal an amount of a compound of formula (I) as defined above, or a salt, hydrate or solvate thereof, effective to inhibit said HSP90 activity; and (ii) a compound of formula (I) as defined above, or a salt hydrate or solvate thereof, for use in human or veterinary medicine, particularly in the treatment of diseases or conditions mediated by excessive or inappropriate HSP90 activity;

It will be understood that the specific dose level for any particular patient will depend upon a variety of factors including the activity of the specific compound employed, the age, body weight, general health, sex, diet, time of administration, route of administration, rate of excretion, drug combination and the causative mechanism and severity of the particular disease undergoing therapy. In general, a suitable dose for orally administrable formulations will usually be in the range of 0.1 to 3000 mg once, twice or three times per day, or the equivalent daily amount administered by infusion or other routes. However, optimum dose levels and frequency of dosing will be determined by clinical trials as is conventional in the art.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

The following examples illustrate the preparation and activities of specific compounds of the invention.

Example 1

1-(2,4-Dihydroxy-phenyl)-5-(4-fluoro-phenyl)-1H-[1,2,3]triazole-4-carboxylic acid

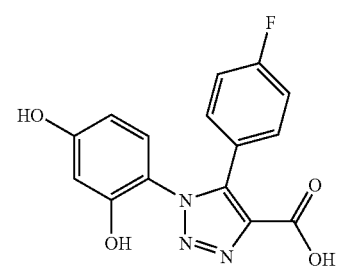

Step 1

1-Azido-5-chloro-2,4-dimethoxy-benzene

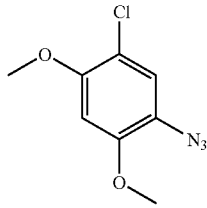

To a solution of concentrated H₂SO₄ (5 mL) in water (15 mL), 5-chloro-2,4-dimethoxy-phenylamine (3 g, 16 mmol) was added, resulting a deep purple suspension. More water (15 mL) was then added and the mixture was cooled and stirred vigorously at 0° C. in an ice-salt bath. A solution of sodium nitrite (1.2 g, 17.4 mmol) in water (5 mL) was added slowly and a brown solution was obtained. This solution was stirred at this temperature for an hour. After that, a solution of sodium azide (1.2 g, 18.5 mmol) in water (10 mL) was followed and the solution turned grey. This solution was then stirred for an hour. The grey precipitations (1.0 g, 30%) formed were collected, washed with water and dried. Yellow solids formed in the filtrate were also collected, washed and dried. The second crop (1.47 g, 43%) turned to light grey quickly.

¹H NMR (d₆-acetone): 6.98 (1H, s); 6.89 (1H, s); 3.95 (3H, s) and 3.92 (3H, s)

Step 2

1-(5-Chloro-2,4-dimethoxy-phenyl)-5-(4-fluoro-phenyl)-1H-[1,2,3]triazole-4-carboxylic acid

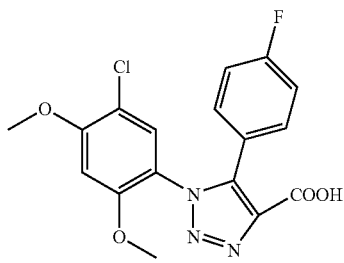

1-Azido-5-chloro-2,4-dimethoxy-benzene (0.4 g, 1.9 mmol), 3-(4-Fluoro-phenyl)-3-oxo-propionic acid methyl ester (0.42 g, 2.2 mmol) and sodium ethoxide in EtOH (70 mg of sodium in 15 mL EtOH) were refluxed for 3 hours. During the reaction, the solution turned brown from dark green. After that, EtOH was evaporated off and the resulting oil was dried in vacuum. Trituration with ether (15 mL) gave light brown solids, which were removed by filtration and washed with ether. The solids then re-dissolved in CHCl₃ and filtered. After evaporation of the solvent, light brown solids were obtained (0.35 g, 50%).

¹H NMR (CDCl₃): 7.20 (1H, s, masked by solvent peak); 7.10 (2H, m); 6.70 (2H, m); 6.20 (1H, s); 3.78 (3H, s) and 3.20 (3H, s)

LC retention time 6.98 minutes [M+H]⁺ 378.1 & 380.1 (3:1)

Step 3

1-(2,4-Dihydroxy-phenyl)-5-(4-fluoro-phenyl)-1H-[1,2,3]triazole-4-carboxylic acid

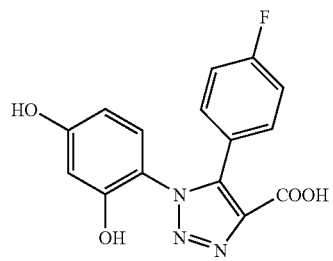

1-(5-Chloro-2,4-dimethoxy-phenyl)-5-(4-fluoro-phenyl)-1H-[1,2,3]triazole-4-carboxylic acid (0.29 g, 0.77 mmol) was refluxed in a mixture of hydroiodic acid (5 mL), acetic acid (1 mL) and acetic anhydride (0.5 mL) for 16 hours. When cooled, water (20 mL) was added and the aqueous layer was extracted with EtOAc (2×15 mL). The combined organic layers were washed with saturated sodium thiosulphate solution (2×15 mL) and brine (20 mL), dried with NaSO₄ and filtered. After evaporation of the solvent, light brown solids were obtained (0.15 g, 62%). The compound was used in the next synthetic step without further purification.

¹H NMR (d₆-acetone): 7.48 (2H, dd, J=9.0 and 5.4 Hz); 7.23 (1H, dm); 7.12 (2H, dd, J=9.0 and 8.8 Hz); 6.46 (1H, d, J=0.6 Hz) and 6.44 (1H, dd, 8.5 and 2.5 Hz)

LC retention time 5.58 minutes [M+H]⁺ 316.1

Example 2

1-(2,4-Dihydroxy-phenyl)-5-(4-fluoro-phenyl)-1H-[1,2,3]triazole-4-carboxylic acid ethyl ester

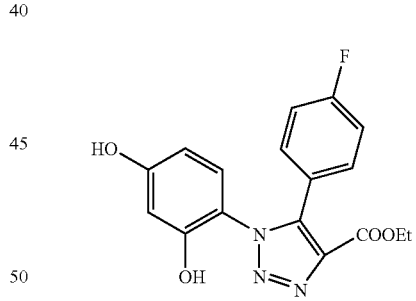

1-(2,4-Dihydroxy-phenyl)-5-(4-fluoro-phenyl)-1H-[1,2,3]triazole-4-carboxylic acid (0.15 g, 0.48 mmol) was refluxed in EtOH (20 mL) in the presence of 5 drops of concentrated H₂SO₄ for 3 hours. After evaporation of the solvent, EtOAc (20 mL) was added. The organic layer was then washed with sat. NaHCO₃ (2×10 mL) and brine (20 mL), dried with NaSO₄ and filtered. After evaporation of the solvent, light brown semi-solids (93 mg, 57%) were obtained and purified by prep. TLC (R_f=0.73, EtOAc).

¹H NMR (d₆-acetone): 8.90 (1H, s, broad); 7.46 (2H, dd, J=9.0 and 5.4 Hz); 7.20 (1H, dd, J=8.6 and 0.8 Hz); 7.12 (2H, dd, J=9.0 and 8.9 Hz); 6.46 (1H, d, J=0.8 Hz); 6.44 (1H, dd, 8.6 and 2.5 Hz); 4.25 (2H, q, J=7.0 Hz) and 1.20 (3H, t, J=7.0 Hz)

LC retention time 6.58 minutes [M+H]⁺ 344.1

Example 3

1-(5-Chloro-2,4-dihydroxy-phenyl)-5-(4-fluoro-phenyl)-1H-[1,2,3]triazole-4-carboxylic acid ethyl ester

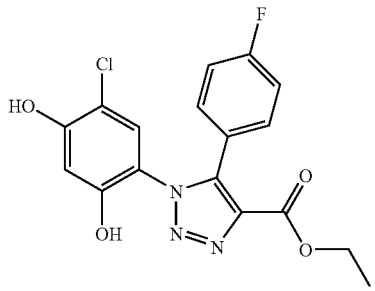

Method:

1-(5-Chloro-2-hydroxy-4-methoxy-phenyl)-5-(4-fluoro-phenyl)-1H-[1,2,3]triazole-4-carboxylic acid ethyl ester and 1-(5-Chloro-2,4-dihydroxy-phenyl)-5-(4-fluoro-phenyl)-1H-[1,2,3]triazole-4-carboxylic acid ethyl ester

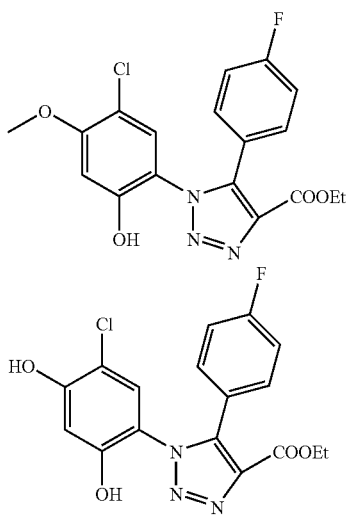

1-(5-Chloro-2,4-dimethoxy-phenyl)-5-(4-fluoro-phenyl)-1H-[1,2,3]triazole-4-carboxylic acid (38 mg) was refluxed in HBr (48%, 1 mL) and acetic acid (1 mL) for 16 hours. When cooled, water (10 mL) was added and the aqueous layer was extracted with EtOAc (2×10 mL). The combined organic layers were then washed with brine (2×10 mL), dried with $NaSO_4$ and filtered. After evaporation of the solvent, the crude acid mixture was dried in vacuum and used in the next step. $^1$Hnmr and LCMS of the crude mixture were analysed. EtOH (6 mL) and 3 drops of concentrated $H_2SO_4$ were added to the above acid mixture and refluxed for 2 hours. After evaporation of the solvent, EtOAc (10 mL) was added. The organic layer was then washed with sat. $NaHCO_3$ (2×10 mL) and brine (2×10 mL), dried with $NaSO_4$ and filtered. After evaporation of the solvent, the esters were purified by prep. TLC. The mono-methoxy compound has $R_f$=0.52 whereas the dihydroxy compound has $R_f$=0.35 (EtOAc:n-hexane/3:2).

The mono-methoxy compound:

$^1$H NMR ($d_6$-acetone): 7.61 (1H, s); 7.45 (2H, dd, J=9.0 and 5.4 Hz); 7.16 (2H, dd, J=9.0 and 8.8 Hz); 6.72 (1H, s); 4.25 (2H, q, J=7.0 Hz); 3.56 (3H, s); and 1.22 (3H, t, J=7 Hz)

LC retention time 7.24 minutes [M−H]⁻ 390.2 & 392.1 (3:1)

The dihydroxy compound (Example 3)

$^1$Hnmr ($d_6$-acetone): 7.50 (2H, dd, J=9.0 and 5.4 Hz); 7.48 (1H, s); 7.16 (2H, dd; J=9.0 and 8.8 Hz); 6.66 (1H, s); 4.25 (2H, q, J=7.0 Hz); and 1.22 (3H, t, J=7 Hz)

LC retention time 7.10 minutes [M+H]⁺ 378.1 & 380.1 (3:1)

The compounds of Examples 1-3 above were tested in the fluorescence polarisation assay described below in the Assay section and the results are as shown in the following Table. Also tested were a number of commercially available compounds having structures with which the invention is concerned (Examples (i)-(v) in the Table). The suppliers of these commercially available compounds were Asinex Ltd (6, Schukinskaya Street, Moscow 123182, Russia) and Interbioscreen Ltd (Institutsky Prospect 7a, 142432 Chemogolovka, Russia).

| Example | Structure | MH+ | Hsp90 IC50 | Source |
|---------|-----------|-----|------------|--------|
| (i) | 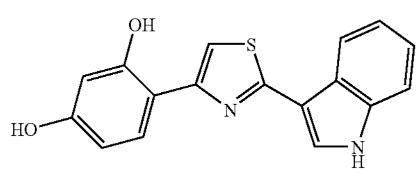 | 309 | B | Asinex |
| (ii) | 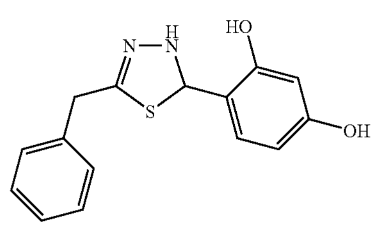 | 287 | B | Asinex |

-continued

| Example | Structure | MH+ | Hsp90 IC50 | Source |
|---|---|---|---|---|
| (iii) | 2,4-dihydroxyphenyl-substituted 3-mercapto-4-(naphthalen-1-yl)-4H-1,2,4-triazole | 336 | A | Interbioscreen |
| (iv) | 2,4-dihydroxyphenyl-substituted 3-mercapto-4-(o-tolyl)-4H-1,2,4-triazole | 300 | A | Interbioscreen |
| (v) | 2,4-dihydroxyphenyl-substituted 3-mercapto-4-(2,5-dimethoxyphenyl)-4H-1,2,4-triazole | 346 | A | Interbioscreen |
| Example 1 | 1-(2,4-dihydroxyphenyl)-5-(4-fluorophenyl)-1H-1,2,3-triazole-4-carboxylic acid | 350 | B | |
| Example 2 | ethyl 1-(2,4-dihydroxyphenyl)-5-(4-fluorophenyl)-1H-1,2,3-triazole-4-carboxylate | 344 | B | |

-continued

| Example | Structure | MH+ | Hsp90 IC50 | Source |
|---|---|---|---|---|
| Example 3 | 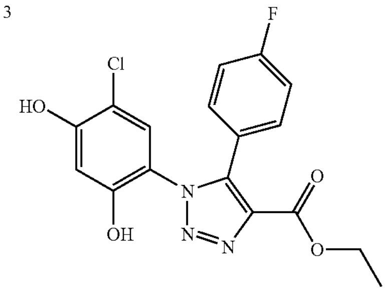 | 378 | A | |

Assay

A fluorescence polarization assay was employed for the evaluation of some of the compounds of the Examples:

Fluorescence Polarization Assay

Fluorescence polarization {also known as fluorescence anisotropy} measures the rotation of a fluorescing species in solution, where the larger molecule the more polarized the fluorescence emission. When the fluorophore is excited with polarized light, the emitted light is also polarized. The molecular size is proportional to the polarization of the fluorescence emission.

The fluoroscein-labelled probe—RBT0045864-FAM—

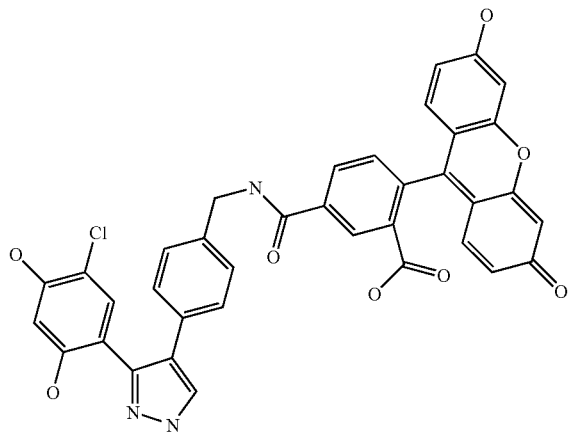

binds to HSP90 {full-length human, full-length yeast or N-terminal domain HSP90} and the anisotropy {rotation of the probe:protein complex} is measured.

Test compound is added to the assay plate, left to equilibrate and the anisotropy measured again. Any change in anisotropy is due to competitive binding of compound to HSP90, thereby releasing probe.

Materials

Chemicals are of the highest purity commercially available and all aqueous solutions are made up in AR water.
1) Costar 96-well black assay plate #3915
2) Assay buffer of (a)100 mM Tris pH7.4; (b) 20 mM KCl; (c) 6 mM MgCl$_2$. Stored at room temperature.
3) BSA (bovine serum albumen) 10 mg/ml (New England Biolabs #B9001S)
4) 20 mM probe in 100% DMSO stock concentration. Stored in the dark at RT. Working concentration is 200 nM diluted in AR water and stored at 4° C. Final concentration in assay 80 nM.
5) *E. coli* expressed human full-length HSP90 protein, purified >95% (see, e.g., Panaretou et al., 1998) and stored in 50 μL aliquots at −80° C.

Protocol

1) Add 100 μl 1× buffer to wells 11A and 12A (=FP BLNK)
2) Prepare assay mix—all reagents are kept on ice with a lid on the bucket as the probe is light-sensitive.

| | | i. Final Conc" |
|---|---|---|
| 1× Hsp90 FP Buffer | 10 ml | 1× |
| BSA 10 mg/ml (NEB) | 5.0 μl | 5 μg/ml |
| Probe 200 μM | 4.0 μl | 80 nM |
| Human full-length Hsp90 | 6.25 μl | 200 nM |

3) Aliquot 100 μl assay mix to all other wells
4) Seal plate and leave in dark at room temp for 20 minutes to equilibrate Compound Dilution Plate—1×3 Dilution Series 1) In a clear 96-well v-bottom plate—{#VWR 007/008/257} add 10 μl 100% DMSO to wells B1 to H11
2) To wells A1 to A11 add 17.5 μl 100% DMSO
3) Add 2.5 μl cpd to A1. This gives 2.5 mM {50×} stock cpd—assuming cpds 20 mM.
4) Repeat for wells A2 to A10. Control in columns 11 and 12.
5) Transfer 5 μl from row A to row B—not column 12. Mix well.
6) Transfer 5 μl from row B to row C. Mix well.
7) Repeat to row G.
8) Do not add any compound to row H—this is the 0 row.
9) This produces a 1×3 dilution series from 50 μM to 0.07 μM.
10) In well B12 prepare 20 μl of 100 μM standard compound.
11) After first incubation the assay plate is read on a Fusion™ α-FP plate reader (Packard BioScience, Pangbourne, Berkshire, UK).
12) After the first read, 2 μl of diluted compound is added to each well for columns 1 to 10. In column 11 {provides standard curve} only add compound B11-H11. Add 2 µl of 100 mM standard cpd to wells B12-H12 {is positive control}

13) The Z' factor is calculated from zero controls and positive wells. It typically gives a value of 0.7-0.9.

The compounds tested in the above assay were assigned to one of two activity ranges, namely A=<10 µM; B=>10 µM, and those assignments are reported above.

REFERENCES

Argon Y and Simen B B. 1999 "Grp94, an ER chaperone with protein and peptide binding properties", *Semin. Cell Dev. Biol.*, Vol. 10, pp. 495-505.

Bijlmakers M-J J E, Marsh M. 2000 "Hsp90 is essential for the synthesis and subsequent membrane association, but not the maintenance, of the Src-kinase p 56lck", *Molecular Biology of the Cell*, Vol. 11 (5), pp. 1585-1595.

Bucci M; Roviezzo F; Cicala C; Sessa W C, Cirino G. 2000 "Geldanamycin, an inhibitor of heat shock protein 90 (Hsp90) mediated signal transduction has anti-inflammatory effects and interacts with glucocorticoid receptor in vivo", *Brit. J. Pharmacol., Vol* 131 (1), pp. 13-16.

Chen C-F, Chen Y, Dai K D, Chen P-L, Riley D J and Lee W-H. 1996 "A new member of the hsp90 family of molecular chaperones interacts with the retinoblastoma protein during mitosis and after heat shock", *Mol. Cell. Biol.*, Vol. 16, pp. 4691-4699.

Chiosis G, Timaul M N, Lucas. B, Munster P N, Zheng F F, Sepp-Lozenzino L and Rosen N. 2001 "A small molecule designed to bind to the adenine nucleotide pocket of HSP90 causes Her2 degradation and the growth arrest and differentiation of breast cancer cells", *Chem. Biol.*, Vol. 8, pp. 289-299.

Conroy S E and Latchman D S. 1996 "Do heat shock proteins have a role in breast cancer?", *Brit. J. Cancer*, Vol. 74, pp. 717-721.

Felts S J, Owen B A L, Nguyen P, Trepel J, Donner D B and Toft D O. 2000 "The HSP90-related protein TRAP1 is a mitochondrial protein with distinct functional properties", *J. Biol. Chem.*, Vol. 5, pp. 3305-3312.

Fuller W, Cuthbert A W. 2000 "Post-translational disruption of the delta F508 cystic fibrosis transmembrane conductance regulator (CFTR)-molecular Chaperone complex with geldanamycin stabilizes delta F508 CFTR in the rabbit reticulocyte lysate", *J. Biol. Chem.*; Vol 275(48), pp. 37462-37468.

Hickey E, Brandon S E, Smale G, Lloyd D and Weber L A. 1999 "Sequence and regulation of a gene encoding a human 89-kilodalton heat shock protein", *Mol. Cell. Biol.*, Vol. 9, pp. 2615-2626.

Hoang A T, Huang J, Rudra-Gonguly N, Zheng J, Powell W C, Rabindron S K, Wu C and Roy-Burman P. 2000 "A novel association between the human heat shock transcription factor I (HSF1) and prostate adenocarcinoma, *Am. J. Pathol.*, Vol. 156, pp. 857-864.

Hostein I, Robertson D, Di Stefano F, Workman P and Clarke P A. 2001 "Inhibition of signal transduction by the HSP90 inhibitor 17-allylamino-17-demethoxygeldanamycin results in cytostasis and apoptosis", *Cancer Res.*, Vol. 61, pp. 4003-4009.

Hur E, Kim H-H, Choi S M, Kim J H, Yim S, Kwon H J, Choi Y, Kim D K, Lee M-O, Park H. 2002 "Reduction of hypoxia-induced transcription through the repression of hypoxia-inducible factor-1α/aryl hydrocarbon receptor nuclear translocator DNA binding by the 90-kDa heat-shock protein inhibitor radicicol", *Mol. Pharmacol.*, Vol 62(5), pp. 975-982.

Hutter et al, 1996, *Circulation*, Vol. 94, pp. 1408.

Jameel A, Skilton R A, Campbell T A, Chander S K, Coombes R C and Luqmani Y A. 1992 "Clinical and biological significance of HSP89a in human breast cancer", *Int. J. Cancer*, Vol. 50, pp. 409-415.

Jolly C and Morimoto R I. 2000 "Role of the heat shock response and molecular chaperones in oncogenesis and cell death", *J. Natl. Cancer Inst.*, Vol. 92, pp. 1564-1572.

Kawanishi K, Shiozaki H, Doki Y, Sakita t, Inoue M, Yano M, Tsujinata T, Shamma A and Monden M. 1999 "Prognostic significance of heat shock proteins 27 and 70 in patients with squamous cell carcinoma of the esophagus", *Cancer*, Vol. 85, pp. 1649-1657.

Kelland L R, Abel G, McKeage M J, Jones M, Goddard P M, Valenti M, Murrer B A and Harrap K R. 1993 "Preclinical antitumour evaluation of bis-acetalo-amino-dichloro-cyclohexylamine platinum (IV): an orally active platinum drug", *Cancer Research*, Vol. 53, pp. 2581-2586.

Kelland L R, Sharp S Y, Rogers P M, Myers T G and Workman P. 1999 "DT-diaphorase expression and tumor cell sensitivity to 17-allylamino, 17-demethoxygeldanamycin, an inhibitor of heat shock protein 90", *J. Natl. Cancer Inst.*, Vol. 91, pp. 1940-1949.

Kurebayashi J, Otsuki T, Kurosumi M, Soga S, Akinaga S, Sonoo, H. 2001 "A radicicol derivative, KF58333, inhibits expression of hypoxia-inducible factor-1α and vascular endothelial growth factor, angiogenesis and growth of human breast cancer xenografts", *Jap. J. Cancer Res.*, Vol 92(12), 1342-1351.

Kwon H J, Yoshida M, Abe K, Horinouchi S and Bepple T. 1992 "Radicicol, an agent inducing the reversal of transformed phentoype of src-transformed fibroblasts, *Biosci., Biotechnol., Biochem.*, Vol. 56, pp. 538-539.

Lebeau J, Le Cholony C, Prosperi M T and Goubin G. 1991 "Constitutive overexpression of 89 kDa heat shock protein gene in the HBL100 mammary cell line converted to a tumorigenic phenotype by the EJ/T24 Harvey-ras oncogene", *Oncogene*, Vol. 6, pp. 1125-1132.

Marcu M G, Chadli A, Bouhouche I, Catelli M and Neckers L. 2000a "The heat shock protein 90 antagonist novobiocin interacts with a previously unrecognized ATP-binding domain in the carboxyl terminus of the chaperone", *J. Biol. Chem.*, Vol. 275, pp. 37181-37186.

Marcu M G, Schulte T W and Neckers L. 2000b "Novobiocin and related coumarins and depletion of heat shock protein 90-dependent signaling proteins", *J. Natl. Cancer Inst.*, Vol. 92, pp. 242-248.

Martin K J, Kritzman B M, Price L M, Koh B, Kwan C P, Zhang X, MacKay A, O'Hare M J, Kaelin C M, Mutter G L, Pardee A B and Sager R. 2000 "Linking gene expression patterns to therapeutic groups in breast cancer", *Cancer Res.*, Vol. 60, pp. 2232-2238.

Neckers L, Schulte T W and Momnaaugh E. 1999 "Geldanamycin as a potential anti-cancer agent: its molecular target and biochemical activity", *Invest. New Drugs*, Vol. 17, pp. 361-373.

Page J, Heath J, Fulton R, Yalkowsky E, Tabibi E, Tomaszewski J, Smith A and Rodman L. 1997 "Comparison of geldanamycin (NSC-122750) and 17-allylaminogeldanamycin (NSC-330507D) toxicity in rats", *Proc. Am. Assoc. Cancer Res.*, Vol. 38, pp. 308.

Panaretou B, Prodromou C, Roe S M, O'Brien R, Ladbury J E, Piper P W and Pearl L H. 1998 "ATP binding and hydrolysis are essential to the function of the HSP90 molecular chaperone in vivo", *EMBO J.*, Vol. 17, pp. 4829-4836.

Plumier et al, 1997, *Cell. Stress Chap.*, Vol. 2, pp. 162

Pratt W B. 1997 "The role of the HSP90-based chaperone system in signal transduction by nuclear receptors and receptors signalling via MAP kinase", *Annu. Rev. Pharmacol. Toxicol.*, Vol. 37, pp. 297-326.

Prodromou C and Pearl L H. 2000a "Structure and in vivo function of HSP90", *Curr. Opin. Struct. Biol.*, Vol. 10, pp. 46-51.

Prodromou C, Roe S M, O'Brien R, Ladbury J E, Piper P W and Pearl L H. 1997 "Identification and structural characterization of the ATP/ADP-binding site in the HSP90 molecular chaperone", *Cell*, Vol. 90, pp. 65-75.

Prodromou C, Panaretou B, Chohan S, Siligardi G, O'Brien R, Ladbury J E, Roe S M, Piper P W and Pearl L H. 2000b "The ATPase cycle of HSP90 drives a molecular 'clamp' via transient dimerization of the N-terminal domains", *EMBO J.*, Vol. 19, pp. 4383-4392.

Rajder et al, 2000, *Ann. Neurol.*, Vol. 47, pp. 782.

Roe S M, Prodromou C, O'Brien R, Ladbury J E, Piper P W and Pearl L H. 1999 "Structural basis for inhibition of the HSP90 molecular chaperone by the antitumour antibiotics radicicol and geldanamycin", *J. Med. Chem.*, Vol. 42, pp. 260-266.

Rutherford S L and Lindquist S. 1998 "HSP90 as a capacitor for morphological evolution. *Nature*, Vol. 396, pp. 336-342.

Schulte T W, Akinaga S, Murakata T, Agatsuma T, Sugimoto S, Nakano H, Lee Y S, Simen B B, Argon Y, Felts S, Toft D O, Neckers L M and Sharma S V. 1999 "Interaction of radicicol with members of the heat shock protein 90 family of molecular chaperones", *Mol. Endocrinology*, Vol. 13, pp. 1435-1448.

Schulte T W, Akinaga S, Soga S, Sullivan W, Sensgard B, Toft D and Neckers L M. 1998 "Antibiotic radicicol binds to the N-terminal domain of HSP90 and shares important biologic activities with geldanamcyin", *Cell Stress and Chaperones*, Vol. 3, pp. 100-108.

Schulte T W and Neckers L M. 1998 "The benzoquinone ansamycin 17-allylamino-17-deemthoxygeldanamcyin binds to HSP90 and shares important biologic activities with geldanamycin", *Cancer Chemother. Pharmacol.*, Vol. 42, pp. 273-279.

Sittler et al, 2001, *Hum. Mol. Genet.*, Vol. 10, pp. 1307.

Smith D F. 2001 "Chaperones in signal transduction", in: *Molecular chaperones in the cell* (P Lund, ed.; Oxford University Press, Oxford and NY), pp. 165-178.

Smith D F, Whitesell L and Katsanis E. 1998 "Molecular chaperones: Biology and prospects for pharmacological intervention", *Pharmacological Reviews*, Vol. 50, pp. 493-513.

Song H Y, Dunbar J D, Zhang Y X, Guo D and Donner D B. 1995 "Identification of a protein with homology to hsp90 that binds the type 1 tumour necrosis factor receptor", *J. Biol. Chem.*, Vol. 270, pp. 3574-3581.

Stebbins C E, Russo A, Schneider C, Rosen N, Hartl F U and Pavletich N P. 1997 "Crystal structure of an HSP90-geldanamcyin complex: targeting of a protein chaperone by an antitumor agent", *Cell*, Vol. 89, pp. 239-250.

Supko J G, Hickman R L, Grever M R and Malspeis L. 1995 "Preclinical pharmacologic evaluation of geldanamycin as an antitumour agent", *Cancer Chemother. Pharmacol.*, Vol. 36, pp. 305-315.

Tratzelt et al, 1995, *Proc. Nat. Acad. Sci.*, Vol. 92, pp. 2944.

Trost et al, 1998, *J. Clin. Invest.*, Vol. 101, pp. 855.

Tytell M and Hooper P L. 2001 "Heat shock proteins: new keys to the development of cytoprotective therapies", *Emerging Therapeutic Targets*, Vol. 5, pp. 267-287.

Uehara U, Hori M, Takeuchi T and Umezawa H. 1986 "Phenotypic change from transformed to normal induced by benzoquinoid ansamycins accompanies inactivation of p60src in rat kidney cells infected with Rous sarcoma virus", *Mol. Cell. Biol.*, Vol. 6, pp. 2198-2206.

Waxman, Lloyd H. Inhibiting hepatitis C virus processing and replication. (Merck & Co., Inc., USA). PCT Int. Appl. (2002), WO 0207761

Winklhofer et al, 2001, *J. Biol. Chem.*, Vol. 276, 45160.

Whitesell L, Mimnaugh E G, De Costa B, Myers C E and Neckers L M. 1994 "Inhibition of heat shock protein HSP90-pp60v-src heteroprotein complex formation by benzoquinone ansamycins: essential role for stress proteins in oncogenic transformation", *Proc. Natl. Acad. Sci. U.S. A.*, Vol. 91, pp. 8324-8328.

Yorgin et al. 2000 "Effects of geldanamycin, a heat-shock protein 90-binding agent, on T cell function and T cell nonreceptor protein tyrosine kinases", *J. Immunol.*, Vol 164(6), pp. 2915-2923.

Young J C, Moarefi I and Hartl F U. 2001 "HSP90: a specialized but essential protein-folding tool", *J. Cell. Biol.*, Vol. 154, pp. 267-273.

Zhao J F, Nakano H and Sharma S. 1995 "Suppression of RAS and MOS transformation by radicicol", *Oncogene*, Vol. 11, pp. 161-173.

The invention claimed is:

1. A compound of formula (IE) or a salt or N-oxide thereof:

wherein $R_1$ has the formula (IIA):

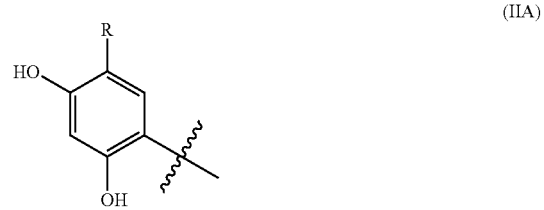

wherein R represents bromo, chloro, phenyl, $C_1$-$C_6$ alkyl or phenyl($C_1$-$C_6$ alkyl)

$R_2$ is hydrogen or a carboxamide radical of formula $CONR^B(Alk)_nR^A$, wherein Alk is an optionally substituted divalent alkylene, alkenylene or alkynylene radical; n is 0 or 1; $R^B$ is hydrogen or a $C_1$-$C_6$ alkyl or $C_2$-$C_6$ alkenyl group; $R^A$ is hydroxy or an optionally substituted carbocyclic or heterocyclic ring; or $R^A$ and $R^B$ taken together with the nitrogen to which they are attached form an N-heterocyclic ring which may optionally contain one or more additional hetero atoms selected from O, S and N, and which may optionally be substituted on one or more ring C or N atoms; or a non aromatic carbocyclic or non aromatic heterocyclic ring wherein a ring carbon is optionally substituted, and/or a ring nitrogen is optionally substituted by a group of formula -(Alk$^1$)$_p$-(Z)$_r$-(Alk$^2$)$_s$-Q wherein in any compatible combination Alk$^1$ and Alk$^2$ are divalent $C_1$-$C_6$ alkylene or $C_2$-$C_6$ alkenylene radicals, p, r and s are independently 0 or 1, Z is —O—, —S—, —(C=O)—, —(C=S)—, —SO$_2$—, —C(=O)O—, —C(=O)NR$^A$—, —C(=S)NR$^A$—; —SO$_2$NR$^A$, —NR$^A$C(=O)—, —NR$^A$SO$_2$— or —NR$^A$— wherein R$^A$ is hydrogen or $C_1$-$C_6$ alkyl, and Q is hydrogen or a carbocyclic or heterocyclic radical;

wherein each of Alk$^1$, Alk$^2$, and Q are optionally substituted with one or more substituents selected from ($C_1$-$C_6$)alkyl, ($C_1$-$C_6$)alkoxy, hydroxy, hydroxy($C_1$-$C_6$)alkyl, mercapto, mercapto($C_1$-$C_6$)alkyl, ($C_1$-$C_6$)alkylthio, halo (including fluoro and chloro), trifluoromethyl, trifluoromethoxy, nitro, nitrile (—CN), oxo, phenyl, —COOH, COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$, or —NR$^A$CONR$^A$R$^B$, wherein R$^A$ and R$^B$ are independently a ($C_1$-$C_6$)alkyl group; and R$_3$ is hydrogen, optionally substituted cycloalkyl, cycloalkenyl, $C_1$-$C_6$ alkyl, $C_2$-$C_6$ alkenyl, or $C_2$-$C_6$alkynyl; or a carboxyl, carboxamide or carboxyl ester group, PROVIDED THAT at least one of R$_2$ and R$_3$ is present and is other than hydrogen.

2. The compound as claimed in claim 1 wherein

Alk is an optionally substituted —CH$_2$—, —CH$_2$CH$_2$—, —CH$_2$CH$_2$CH$_2$—, CH$_2$CH=CH—, or CH$_2$CCCH$_2$— radical, n is 0 or 1, R$^B$ is hydrogen, methyl, ethyl, n- or iso-propyl, or allyl, R$^A$ is hydroxy, hydroxy and/or chloro-substituted phenyl, 3,4 methylenedioxyphenyl, pyridyl, furyl, thienyl, N-piperazinyl, or Nmorpholinyl, or R$^A$ and R$^B$ taken together with the nitrogen to which they are attached form a morpholino, piperidinyl, piperazinyl or N-phenylpiperazinyl ring.

3. The compound as claimed in claim 1 wherein n is 0, R$^B$ is hydrogen and R$^A$ is hydroxy or an optionally substituted carbocyclic or heterocyclic ring.

4. The compound as claimed in claim 1 wherein R$_3$ is hydrogen, methyl, ethyl, n- or iso-propyl, trifluoromethyl, or hydroxyethyl.

5. The compound as claimed in claim 1 wherein R$_3$ is a carboxamide group —CONR$^B$(Alk)$_n$R$^A$ wherein Alk is an optionally substituted divalent alkylene, alkenylene or alkynylene radical, n is 0 or 1, R$^B$ is hydrogen or a $C_1$-$C_6$ alkyl or $C_2$-$C_6$ alkenyl group, R$^A$ is hydroxy or an optionally substituted carbocyclic or heterocyclic ring, or R$^A$ and R$^B$ taken together with the nitrogen to which they are attached form an N-heterocyclic ring which may optionally contain one or more additional hetero atoms selected from O, S and N, and which may optionally be substituted on one or more ring C or N atoms.

6. A pharmaceutical or veterinary composition comprising a compound as defined in claim 1, or a salt thereof, together with a pharmaceutically or veterinarily acceptable carrier.

* * * * *